(12) United States Patent
Kobayashi

(10) Patent No.: US 9,500,647 B2
(45) Date of Patent: Nov. 22, 2016

(54) FLUIDIC DEVICE, TESTING DEVICE, AND METHOD FOR FABRICATING FLUIDIC DEVICE

(71) Applicant: Rie Kobayashi, Shizuoka (JP)

(72) Inventor: Rie Kobayashi, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 13 days.

(21) Appl. No.: 14/491,415

(22) Filed: Sep. 19, 2014

(65) Prior Publication Data
US 2015/0079668 A1    Mar. 19, 2015

(30) Foreign Application Priority Data

Sep. 19, 2013  (JP) ................................ 2013-194507
Sep. 8, 2014   (JP) ................................ 2014-181887

(51) Int. Cl.

| | | |
|---|---|---|
| *B01L 3/00* | (2006.01) | |
| *G01N 30/92* | (2006.01) | |
| *B32B 37/24* | (2006.01) | |
| *G01N 33/558* | (2006.01) | |
| *G01N 30/00* | (2006.01) | |
| *G01N 30/60* | (2006.01) | |
| *B01D 15/38* | (2006.01) | |
| *G01N 30/02* | (2006.01) | |

(52) U.S. Cl.
CPC ............ *G01N 33/558* (2013.01); *B01L 3/5023* (2013.01); *B01D 15/3804* (2013.01); *B01L 2200/12* (2013.01); *B01L 2300/0654* (2013.01); *B01L 2300/0825* (2013.01); *B01L 2300/126* (2013.01); *B01L 2300/16* (2013.01); *B01L 2400/0406* (2013.01); *G01N 30/02* (2013.01); *G01N 30/6047* (2013.01); *G01N 30/92* (2013.01); *Y10T 156/10* (2015.01)

(58) Field of Classification Search
CPC .. G01N 30/02; G01N 30/6047; G01N 30/92; G01N 33/558; B01D 15/3804; B01L 2300/0654; B01L 2300/0825; B01L 2400/0406; B01L 3/5023
See application file for complete search history.

(56) References Cited

U.S. PATENT DOCUMENTS

| 5,354,692 | A | * | 10/1994 | Yang | .................... | G01N 33/558 422/412 |
|---|---|---|---|---|---|---|
| 6,846,453 | B1 | | 1/2005 | Uesaka et al. | | |
| 2002/0031698 | A1 | * | 3/2002 | Inoue | ................. | H01M 8/0271 429/481 |
| 2003/0026740 | A1 | * | 2/2003 | Staats | ................... | B01L 3/0268 422/503 |
| 2005/0013731 | A1 | * | 1/2005 | Burke | ................. | G01N 33/558 422/400 |
| 2005/0058576 | A1 | * | 3/2005 | Pranis | ................ | B01D 17/0202 436/178 |
| 2007/0160502 | A1 | * | 7/2007 | Hwang | ............ | B01L 3/502707 422/400 |
| 2007/0178521 | A1 | * | 8/2007 | Sakaino | ........... | B01L 3/502753 435/7.1 |
| 2009/0045058 | A1 | * | 2/2009 | Fujita | ................ | B01L 3/502707 204/451 |
| 2009/0291505 | A1 | * | 11/2009 | Sarofim | ............. | B01L 3/50851 436/94 |

(Continued)

FOREIGN PATENT DOCUMENTS

| JP | 4233686 | 12/2008 |
|---|---|---|
| JP | 2009-250763 | 10/2009 |

(Continued)

*Primary Examiner* — Jennifer Wecker
(74) *Attorney, Agent, or Firm* — Oblon, McClelland, Maier & Neustadt, L.L.P.

(57) ABSTRACT

Provided is a fluidic device including: a support member; a porous layer; and an adhesive layer bonding the support member and the porous layer with each other. A partition wall made of a thermoplastic material is formed in the porous layer. The support member has a heatproof temperature that is higher than a melting start temperature of the thermoplastic material.

9 Claims, 3 Drawing Sheets

(56) References Cited

U.S. PATENT DOCUMENTS

2013/0316393 A1* 11/2013 Swanson ............ C12Q 1/04
    435/34
2014/0147346 A1* 5/2014 Chitnis ............ B81C 1/00119
    422/502

FOREIGN PATENT DOCUMENTS

| | | |
|---|---|---|
| JP | 2010-515877 | 5/2010 |
| WO | WO2008/049083 A2 | 4/2008 |
| WO | WO2012/160857 A1 | 11/2012 |

* cited by examiner

FLUIDIC DEVICE, TESTING DEVICE, AND METHOD FOR FABRICATING FLUIDIC DEVICE

BACKGROUND OF THE INVENTION

Field of the Invention

The present invention relates to a fluidic device, a testing device, and a method for fabricating a fluidic device.

Description of the Related Art

Conventionally, in order to perform various operations using a liquid, fluidic devices formed of a porous layer such as a sheet through which a liquid is let to flow for separation, mixing, an analysis, etc. have been used. A reagent for detecting an analyte can be placed in a flow path of the fluidic devices. Therefore, fluidic devices can be used as testing devices such as biochemical sensors for blood testing or DNA testing, and chemical sensors for quality control of foods and beverages.

Recently, it has been known to provide the fluidic devices with a flow path having a desired shape according to the purposes for which the fluidic devices are used, by forming a partition wall in the porous layer such as a sheet. For example, there is disclosed a method for forming a partition wall in the interior of a sheet by printing the shape of the contour of the flow path in the sheet with an inkjet printer using an ultraviolet curable ink, and irradiating the printed ink with ultraviolet (see International Publication No. WO2012/160857). There is also disclosed a method of forming a flow path wall in a portion of a sheet with a polymerized photoresist, in order for the remaining portion of the sheet that is enclosed within the flow path wall to be used as a flow path (see Japanese Patent Application Laid-Open (JP-A) No. 2010-515877).

Further, in the recent years, fluidic devices have been used in simple tests in the fieldworks. Therefore, fluidic devices have been required not to be blown away by a wind easily. Further, in order to perform the test correctly, the flow path has been required not to bend or buckle when a force is applied to the fluidic device. In response to such requests, there is proposed a fluidic device having a housing in which a spreading pad of a porous layer is contained (see Japanese Patent Application Laid-Open (JP-A) No. 2009-250763).

However, large equipment is required for forming a partition wall according to an inkjet method or a polymerized photoresist method using an ink made of an ultraviolet curable resin. Therefore, it is difficult to form a partition wall of a fluidic device on demand at the site of the fieldwork, etc. Moreover, in order to prevent the fluidic device from being blown away or the flow path from being bent, it is necessary to manually contain the flow path formed of a sheet, etc. in a housing, which is bothersome.

SUMMARY OF THE INVENTION

A fluidic device of the present invention includes:

a support member;

a porous layer; and an adhesive layer bonding the support member and the porous layer with each other, wherein a partition wall made of a thermoplastic material is formed in the porous layer, and wherein the support member has a heatproof temperature that is higher than a melting start temperature of the thermoplastic material.

As explained above, the present invention makes it possible to form a partition wall by thermal transfer, by using a support member that has a heatproof temperature higher than the melting start temperature of a thermoplastic material. A thermal transfer apparatus can be smaller in size than an inkjet printer or a photoresist production apparatus. Therefore, it can provide a fluidic device excellent in an on-demand property. Furthermore, a fluidic device can have a weight and stiffness when the support member is bonded with and used together with the porous layer. Therefore, there is an effect that the fluidic device can be prevented from being blown away and that the flow path can be prevented from being bent, even if a housing is not used.

DETAILED DESCRIPTION OF THE INVENTION

An embodiment of the present invention will be explained below with reference to the drawings.

<<Whole Configuration of Embodiment>>

Figure 1:
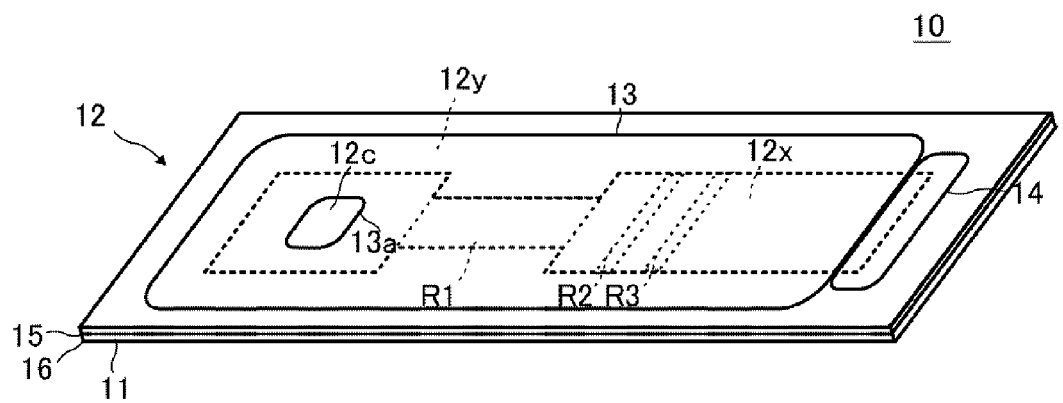
FIG. 1 is a perspective diagram of a testing device according to an embodiment of the present invention.
Figure 2:
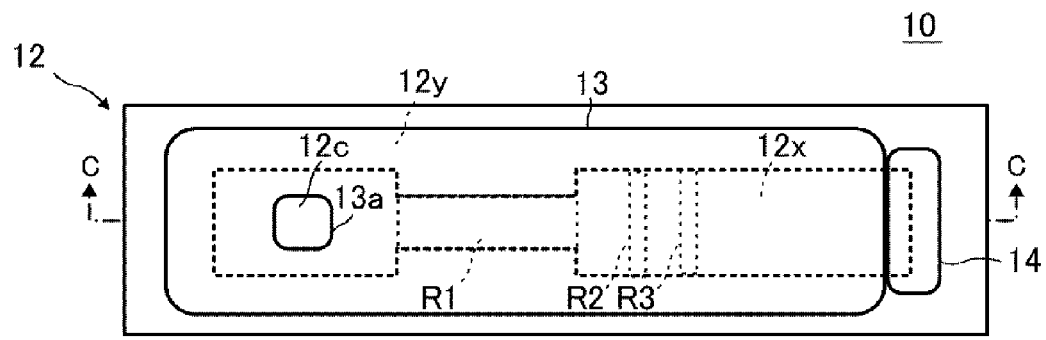
FIG. 2 is a plan view of a testing device according to an embodiment of the present invention.
Figure 3:
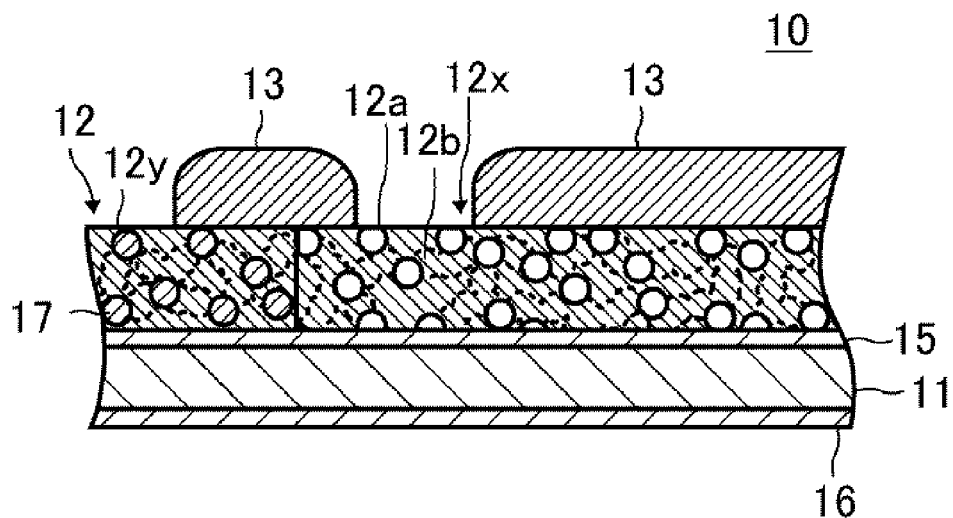
FIG. 3 is a cross-sectional diagram of a testing device according to an embodiment of the present invention.

The whole configuration of an embodiment will be explained with reference to FIG. 1 to FIG. 3. FIG. 1 is a perspective diagram of a testing device according to an embodiment of the present invention. FIG. 2 is a plan view of a testing device according to an embodiment of the present invention. FIG. 3 is a cross-sectional diagram of the testing device of FIG. 2 taken along a line C-C.

The testing device 10 (an example of a fluidic device) shown in FIG. 1 to FIG. 3 includes a base member 11 (an example of a support member), a flow path member 12 (an example of a porous layer), a barrier member 13, an absorbent member 14, an adhesive layer 15, and a viscous layer 16. The adhesive layer 15 bonds the base member 11 and the flow path member 12 with each other. A flow path wall (an example of a partition wall) is formed in the flow path member 12, with pores in the flow path member 12 filled with a thermoplastic flow path wall forming material (an example of a thermoplastic material). The heatproof temperature of the base member 11 is higher than the melting start temperature of the flow path wall forming material. This makes it possible to form a flow path by transferring the flow path wall forming material into the flow path member 12 with a simple apparatus such as a thermal printer, and to thereby form a flow path of a fluidic device on demand at the site, etc. of a fieldwork, etc. In this case, the testing device 10 can have a weight and stiffness, if it is used with the base member 11 bonded and integrated with the flow path member 12. This can prevent the testing device 10 from being blown away or the flow path from being bent, even without a housing.

The melting start temperature of the flow path wall forming material means a flowing start temperature of the flow path wall forming material observed by firstly hardening the flow path wall forming material, introducing it into a cylindrical vessel having an opening with a diameter of 0.5 mm at the bottom, setting the vessel on an elevated flow tester (product name: SHIMADZU FLOW TESTER CFT-100D manufactured by Shimadzu Corporation), raising the temperature of the sample at a constant rate of 5° C./min under a load of a cylinder pressure of 980.7 kPa, and measuring a melt viscosity and a flow property of the sample in accordance with the temperature rise.

The heatproof temperature of the base member 11 is either temperature that is the lower, of a temperature at which the base member starts to thermally deform (Vicat softening point), and a weight reduction start temperature at which the base member starts to thermally decompose. Measurement of a Vicat softening point is performed according to ISO306, by raising an oil temperature of an oil in which the sample is placed at a constant rate of 50° C./h, sticking the sample with a needle having a cross-sectional area of 1 mm$^2$ under a load of 50 N, and measuring the temperature at which the penetration depth reaches 1 mm as a Vicat softening point (VSP). The weight reduction start temperature of the base member 11 is indexed according to thermogravimetric (TG) measurement. Thermogravimetric (TG) measurement is performed according to ISO7111. As the measurement conditions, the sample (10 mg) is precisely weighed out in an aluminum pan, and weight reduction of the sample is measured with a thermobalance at a temperature raising rate of 10° C./min, with a nitrogen gas flown at 250 ml/min. The heatproof temperature is measured as the temperature at which the weight reduction starts. However, weight reduction of attached water is not regarded as the start of weight reduction. It can be said that the heatproof temperature of the base member 11 is higher than the melting start temperature of the flow path wall forming material, when the weight reduction of the base member 11 is less than 3% when the flow path wall forming material is thermally transferred into the flow path member 12. The heatproof temperature of a sheet is typically about 450° C., and a sheet does not thermally deform up until this temperature. Therefore, when a sheet is selected as the base member 11, it can be said that the heatproof temperature of the base member 11 is higher than the melting start temperature of the thermoplastic flow path wall forming material.

When the base member 11 is a material made of a resin, measurement of the specific gravity of the base member 11 is performed according to ISO1183.

As an embodiment of the present invention, a case where an analyte liquid contains water will be explained below. However, the present invention is not limited to this embodiment, and an analyte liquid may contain, for example, an organic solvent. Note that the organic solvent is not particularly limited, and examples thereof include: alcohols such as methyl alcohol, ethyl alcohol, 1-propyl alcohol, and 2-propyl alcohol; and ketones such as acetone and MEK.

In an embodiment, a contact angle between a base member and water can be used as a degree of hydrophilicity or hydrophobicity. In this case, a substance having a large contact angle can be regarded as having a high hydrophobicity. In this case, a substance having a contact angle to water of 45 degrees or less at room temperature can be regarded as hydrophilic, and a substance having a contact angle to water of 60 degrees or greater at room temperature can be regarded as hydrophobic, where the contact angles are measured based on the coordinates on a water droplet image according to an ATAN1/2θ method and a close-up image method based on Young's equation, which is a contact angle measurement model used the most commonly in various fields internationally as a formula for calculating a contact angle (see JIS R 3257).

<<Base Member>>

In an embodiment of the present invention, the flow path member 12 is provided over the base member 11 as shown in FIG. 1 to FIG. 3. The base member 11 is not particularly limited, and any base member that is organic, inorganic, or metallic may be used according to the purpose. It is preferable that at least one side of the base member 11 be provided with a film that imparts water resistance to the base member.

A preferable material of the base member 11 is a sheet of paper. Conventional testing devices need separation of the housing made of aluminum and a spread pad made of paper for disposal. In contrast, the testing device 10 of the present embodiment can be disposed of without separation of the base member 11 and the flow path member 12, when sheets of paper are used as the base member 11 and the flow path member 12 both. A sheet of paper of which at least one side is coated with starch, carboxymethyl cellulose, polyvinyl alcohol, alginic acid, polyacrylamide (PAM), or ketene dimer as a treatment for improving water resistance is particularly preferable. Furthermore, inorganic particles of, for example, talc, kaolin (white bole), calcium carbonate, titanium oxide, and barium sulfate amorphous silica (white carbon) may be added to such a resin. Moreover, a hydrophobic resin may be formed as the film. Examples of such a resin include many such as polyester, polystyrene, a styrene/acrylic copolymer resin, an acrylic resin, polyethylene, polypropylene, and polycarbonate. However, it is not necessarily necessary to impart water resistance by using a structure that has a hydrophobic group. This is because such a material can fill capillary tubes and pores of a sheet and seal them against liquid by being deposited as a film over the surface of the sheet, and because water resistance is by the principle of suppressing water absorption due to capillary flow. Further, a hydrophobic resin film may be pasted over one side of a sheet. In this case, a film made of any of the hydrophobic resins described above can be used.

When the testing device 10 is used as a sensor chip, it is preferable to use a flexible and inexpensive synthetic resin as the base member 11. According to the present embodiment, a base member 11 having a high durability such as a plastic sheet can be selected. As a result, the durability of the testing device 10 will also improve.

Examples of the base member 11 made of a synthetic resin include base members made of polyvinyl chloride, polyethylene terephthalate, polypropylene, polystyrene, polyvinyl acetate, polycarbonate, polyacetal, modified polyphenyl ether, polybutylene phthalate, and an ABS resin. Among these, a base member 11 made of polyethylene terephthalate is particularly preferable because it is inexpensive and versatile.

The shape of the base member 11 is not particularly limited, but a sheet shape is preferable. The average thickness of the base member 11 is not particularly limited and may be appropriately selected according to the purpose. However, it is preferably from 0.1 mm to 1.0 mm. In the present embodiment, the thickness of the measurement target may be measured with a micrometer from a total of 15 positions of the measurement target, namely 5 positions in the longer direction and 3 positions in the width direction that are defined at substantially equal intervals, and the average of the measured values may be used as the average thickness, although this is not particularly limiting. In the present embodiment, the thickness may be the length of the measurement target in the direction perpendicular to the interface at which the base member 11 and the flow path member 12 contact each other. When the average thickness is less than 0.1 mm, the base member 11 may not be able to maintain the strength enough to qualify as a base member. When the average thickness is greater than 1.0 mm, the base member may have insufficient flexibility depending on the material, and may be difficult to use as a sensor.

The basis weight of the base member 11 is not particularly limited, but is preferably 170 g/m² or greater, and more preferably 200 g/m² or greater. When the basis weight is less than 170 g/cm², the testing device 10 may be easily blown away by a wind when the testing device 10 is used for a fieldwork outdoors. When the basis weight of the base member 11 is greater than 200 g/m², it becomes less easy for the testing device 10 to be blown away by a wind, when the testing device 10 is used outdoors without a housing. In an embodiment of the present invention, the testing device 10 does not need a housing. This enables the testing device 10 to be simplified and low-cost.

It is necessary that the heatproof temperature of the base member 11 be higher than the melting start temperature of the flow path wall forming material. When the heatproof temperature of the base member 11 is lower than the melting start temperature of the flow path wall forming material, the base member 11 will thermally deform during formation of the flow path wall by thermal transfer, and will greatly spoil the functionality as a fluidic device of which being smooth is important. Hence, the flow path wall will not satisfy as a flow path wall.

When the adhesive layer 15 is made of a thermoplastic hot-melt adhesive, it is preferable that the heatproof temperature of the base member 11 be higher than the melting start temperature of the adhesive layer 15. When forming a flow path wall by transferring the flow path wall forming material into a filter paper (with a thickness of 100 μm) with a thermal printer, the energy to be applied needs to be from three to four times as high as the energy required when printing on a common rewritable medium or a photosensitive sheet. Therefore, the heatproof temperature of the base member 11 is preferably 150° C. or higher, and more preferably 180° C. or higher. The methods for measuring the heatproof temperature of the base member 11 and the melting start temperature of the flow path wall forming material are as described above.

<<Flow Path Member>>

The flow path member 12 of the testing device 10 is not particularly limited, and examples thereof include a member made of a hydrophilic porous material that is partially hydrophobized to form a pattern for defining a flow path. Such a flow path member 12 includes a porous portion 12*x* that is not hydrophobized, and a flow path wall 12*y* that is hydrophobized, as shown in FIG. 3. The porous portion 12*x* includes pores (12*a* and 12*b*). A flow path is formed when a liquid flows through the pores (12*a* and 12*b*). In FIG. 3, a void 12*a* is a void formed in a cross-section of FIG. 2 taken along a line C-C. A void 12*b* is a void in a deeper portion in the cross-section. It is preferable that cells be present in the hydrophilic porous material, and that the cells be linked and form a continuous cell. A continuous cell is different from independent cells that are not linked. The cells forming a continuous cell have a minute pore in the wall between the cells. Therefore, the continuous cell has a function of absorbing a liquid by means of a capillary action or letting a gas pass through. The flow path member 12 delivers a liquid by utilizing a capillary action. Therefore, an external actuator such as a pump is unnecessary.

Hereinafter, the flow path member 12 before the flow path wall 12*y* is formed therein will be referred to as hydrophilic porous material. The hydrophilic porous material is not particularly limited, and an appropriate one may be selected according to the purpose. A preferable example thereof is a base member having hydrophilicity and a high voidage. A hydrophilic porous material is a porous material into which an aqueous solution can easily penetrate. A material can be said to be easily penetrable, when in a test for water penetrability evaluation, a plate-shaped test piece of the material is dried for 1 hour at 120° C., pure water (0.01 mL) is dropped down onto the surface of the dried test piece, and the pure water (0.01 mL) completely penetrates into the test piece within 10 minutes.

The voidage of the hydrophilic porous material is not particularly limited, and may be appropriately selected according to the purpose. However, it is preferably from 40% to 90%, and more preferably from 65% to 80%. When the voidage is greater than 90%, the hydrophilic porous material may not be able to keep the strength to qualify as a base member. When the voidage is less than 40%, the penetrability of an analyte liquid may be poor.

The voidage can be calculated according to the calculation formula 1 below, based on the basis weight (g/m²) and the thickness (μm) of the hydrophilic porous material, and the specific gravity of the component thereof.

Voidage (%)={1−[basis weight (g/m²)/thickness (μm)/specific gravity of the component]}×100 [Calculation Formula 1]

The hydrophilic porous material is not particularly limited, and an appropriate one may be selected according to the purpose. Examples thereof include filter paper, regular paper, high-quality paper, watercolor paper, Kent paper, synthetic paper, synthetic resin film, special-purpose paper having a coating, fabric, fiber product, film, inorganic substrate, and glass.

Examples of the fabric include artificial fiber such as rayon, bemberg, acetate, nylon, polyester, and vinylon, natural fiber such as cotton and silk, blended fabric of those above, or non-woven fabric of those above.

Among these, filter paper is preferable because it has a high voidage and a favorable hydrophilicity. When the testing device 10 is used as a biosensor, the filter paper is preferable as a stationary phase of paper chromatography.

The shape and average thickness of the hydrophilic porous material are not particularly limited and may be appropriately selected according to the purpose. However, the hydrophilic porous material is preferably a sheet-shaped. The average thickness of the hydrophilic porous material is not particularly limited and may be appropriately selected according to the purpose. However, it is preferably from 0.01 mm to 0.3 mm. When the average thickness is less than 0.01 mm, the hydrophilic porous material may not be able to keep the strength to qualify as a base member. When the average thickness is greater than 0.3 mm, it may be less easy to form a barrier portion described later in the hydrophilic porous material.

The flow path wall 12*y* has hydrophobicity. Hydrophobicity means that the flow path wall is not eroded or destroyed by an aqueous fluid (e.g., an analyte liquid) moving through the flow path of the flow path member 12, or has a barrier property against water. A hydrophobizing method is not particularly limited. Examples thereof include a method of filling the voids of the hydrophilic porous material with, for example, a thermoplastic material, and according to necessity, further with other flow path wall forming materials such as an organic fatty acid, a long-chain alcohol, and other components appropriately selected.

The heatproof temperature of the hydrophilic porous material constituting the flow path member 12 is higher than the melting start temperature of the flow path wall forming materials. Therefore, it is possible to form a flow path by transferring the flow path wall forming materials into the hydrophilic porous material with a simple apparatus such as a thermal printer. Therefore, it is possible to form a flow path of a fluidic device on demand at the site, etc. of a fieldwork, etc. The heatproof temperature of a sheet of paper is typically about 450° C. Therefore, when a sheet of paper is selected as the hydrophilic porous material, it can be said that the heatproof temperature of the hydrophilic porous material is higher than the melting start temperature of the thermoplastic flow path wall forming material.

It is possible to hydrophobize the hydrophilic porous material by transferring the flow path wall forming materials into the hydrophilic porous material, as will be described later. In the following explanation for each of the flow path wall forming materials such as a thermoplastic material, characteristics related with this method will also be explained, where appropriate.

<Thermoplastic Material>

A thermoplastic material for flow path wall formation is not particularly limited, and an appropriate one may be selected according to the purpose, as long as it has durability with which the structure of the testing device 10 is not easily collapsed when it is impregnated with water. For example, the thermoplastic material is preferably at least one selected from fat and oil, and thermoplastic resin.

—Fat and Oil—

The fat and oil means fat, fatty oil, and brazing material that are solid at normal temperature.

The fat and oil is not particularly limited, and appropriate one may be selected according to the purpose. Examples thereof include carnauba wax, paraffin wax, microcrystalline wax, paraffin oxide wax, candelilla wax, montan wax, ceresin wax, polyethylene wax, polyethylene oxide wax, castor wax, beef tallow hardened oil, lanolin, Japan tallow, sorbitan stearate, sorbitan palmitate, stearyl alcohol, polyamide wax, oleylamide, stearylamide, hydroxystearic acid, synthetic ester wax, synthetic alloy wax, and sunflower wax. One of these may be used alone, or two or more of these may be used in combination. Among these, candelilla wax and synthetic ester wax are preferable because they can easily realize formation of the flow path wall 12y.

—Thermoplastic Resin—

The thermoplastic resin is not particularly limited, and an appropriate one may be selected according to the purpose. Examples thereof include polyolefin such as polyethylene and polypropylene, and polyamide-based resin such as polyethylene glycol, polyethylene oxide, acrylic resin, polyester resin, ethylene/vinyl acetate copolymer, ethylene/acrylate copolymer, urethane resin, cellulose, vinyl chloride/vinyl acetate copolymer, petroleum resin, rosin resin, nylon, and copolymer nylon. One of these may be used alone or two or more of these may be used in combination.

Each thermoplastic material may be used as it is, but is preferably contained in the form of an emulsion together with an organic fatty acid and a long-chain alcohol. In this case, when the thermoplastic material is heated by a thermal head, separation preferentially occurs at the boundary between the particles having formed the emulsion, to break away the particles and transfer them into the surface of the hydrophilic porous base member. Therefore, the edge portions of the transferred material become sharp. Further, because the thermoplastic material emulsion is aqueous, it is advantageous in terms of having low environmental impact.

The method for forming an aqueous emulsion of the thermoplastic material is not particularly limited, and an appropriate method may be selected according to the purpose. Examples include a method of emulsifying the thermoplastic material by adding an organic fatty acid and an organic base to water and using the produced salt as an emulsifying agent.

The melting start temperature of the thermoplastic material can be measured in the same method as measuring the melting start temperature of the flow path wall forming material described above.

The melting start temperature of the thermoplastic material means a flowing start temperature that is observed by hardening the thermoplastic material, introducing it into a cylinder-shaped vessel having an opening with a diameter of 0.5 mm in the bottom, setting the vessel on an elevated flow tester (product name: SHIMADZU FLOW TESTER CFT-100D manufactured by Shimadzu Corporation), raising the temperature of the sample at a constant rate of 5° C./min under a load of a cylinder pressure of 980.7 kPa, and measuring the melt viscosity and flow properties of the sample due to the temperature rise.

The content of the thermoplastic material in the flow path wall forming materials is not particularly limited and may be appropriately selected according to the purpose. However, it is preferably 75% by mass or greater. When the content is less than 75% by mass, the sensitivity to heat as a transfer member may be poor.

<Organic Fatty Acid>

The organic fatty acid for flow path wall formation is not particularly limited, and an appropriate one may be selected according to the purpose. However, an organic fatty acid that has a predetermined acid value and a predetermined melting point is preferably used. The acid value of the organic fatty acid is not particularly limited and may be appropriately selected according to the purpose. However, it is preferably from 90 mgKOH/g to 200 mgKOH/g, and more preferably from 140 mgKOH/g to 200 mgKOH/g. When the acid value is less than 90 mgKOH/g, the organic fatty acid may not be able to make an emulsion of the thermoplastic material. When the acid value is greater than 200 mgKOH/g, the organic fatty acid is able to make an emulsion, but may make the emulsion creamy. Therefore, the thermoplastic material may not be prepared as a coating liquid in the production of the transfer member.

The organic fatty acid having an acid value in the range described above is not particularly limited, and an appropriate one may be selected according to the purpose. Examples thereof include oleic acid (with an acid value of 200 mgKOH/g), behenic acid (with an acid value of 160 mgKOH/g), and montanic acid (with an acid value of 132 mgKOH/g).

The acid value can be measured by, for example, dissolving the sample in a mixture solvent of toluene, isopropyl alcohol, and a small amount of water, and titrating the sample with a potassium hydroxide solution.

The melting point of the organic fatty acid is not particularly limited and may be appropriately selected according to the purpose. However, it is preferably from 70° C. to 90° C. When the melting point is within the preferable value range, it is close to the melting start temperature of the thermoplastic material, which makes the sensitivity property favorable. When the melting point is lower than 70° C., the flow path wall 12y may be softened under high-temperature conditions such as summertime.

The organic fatty acid having a melting point in the range described above is not particularly limited, and an appropriate one may be selected according to the purpose. Examples thereof include behenic acid (with a melting point of 76° C.) and montanic acid (with a melting point of 80° C.).

The melting point can be measured by using a differential scanning calorimeter "DSC7020" (manufactured by Seiko Instruments, Inc.) and measuring the temperature at which a crystal melting endothermic peak that is to appear in a temperature raising measurement with the differential scanning calorimeter ends.

The content of the organic fatty acid is not particularly limited and may be appropriately selected according to the purpose. However, it is preferably from 1 part by mass to 6 parts by mass relative to 100 parts by mass of the thermoplastic material. When the content is less than 1 part by mass, the organic fatty acid may not be able to make the thermoplastic material an emulsion, when preparing a coating liquid used for production of the transfer member. When the content is greater than 6 parts by mass, blooming of the thermoplastic material may occur.

<Long-Chain Alcohol>

The long-chain alcohol is not particularly limited, and an appropriate one may be selected according to the purpose. However, at least any selected from a long-chain alcohol represented by General Formula (1) below and a long-chain alcohol represented by General Formula (2) below is preferable.

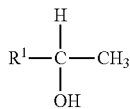

General Formula (1)

In General Formula (1) above, $R^1$ represents an alkyl group having 28 to 38 carbon atoms.

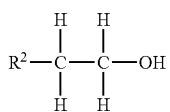

General Formula (2)

In General Formula (2) above, $R^2$ represents an alkyl group having 28 to 38 carbon atoms.

The long-chain alcohol is not particularly limited, and an appropriate one may be selected according to the purpose. However, it is preferably an aliphatic alcohol having a melting point of from 70° C. to 90° C. When the melting point is lower than 70° C., the flow path wall 12y may be softened under high-temperature conditions such as summertime. When the melting point is higher than 90° C., the transferability may be poor. When the melting point is within the preferable value range, it is close to the melting start temperature of the thermoplastic material, which makes the transferability of the transfer member favorable. The melting point can be measured by the same method for measuring the melting point of the organic fatty acid.

The long chain of the long-chain alcohol may be composed only of a straight chain, or may have branched chains. The number of carbon atoms on the long chain (the number of carbon atoms in the alkyl group) is not particularly limited and may be appropriately selected according to the purpose. However, it is preferably from 28 to 38. When the number of carbon atoms is not within the above value range, the transfer member may cause blooming along with the elapse of time, and may contaminate the surroundings when it is stored in a rolled shape.

The content of the long-chain alcohol is not particularly limited and may be appropriately selected according to the purpose. However, it is preferably from 6 parts by mass to 12 parts by mass relative to 100 parts by mass of the thermoplastic material. When the content is less than 6 parts by mass, the blooming suppression effect may not be obtained. When the content is greater than 12 parts by mass, the transferability of the transfer member may be poor when the long-chain alcohol has a temperature difference from the melting start temperature of the thermoplastic material.

<Other Components>

The other components are not particularly limited, and appropriate ones may be selected according to the purpose. Examples thereof include an organic base, a non-ionic surfactant, and a colorant.

—Organic Base—

The organic base may be used together with the organic fatty acid when emulsifying the thermoplastic material.

The organic base is not particularly limited, and an appropriate one may be selected according to the purpose. However, morpholine is preferable because it easily volatilizes after dried. The content of the organic base is not particularly limited and may be appropriately selected according to the purpose. However, it is preferably from 0.5 parts by mass to 5 parts by mass relative to 100 parts by mass of the thermoplastic material.

—Non-Ionic Surfactant—

Addition of the non-ionic surfactant enables the aqueous emulsion of the thermoplastic material to have a small particle diameter, which improves the cohesive force of the flow path wall 12y and enables prevention of a background smear. The non-ionic surfactant is not particularly limited, and an appropriate one may be selected according to the purpose. Examples thereof include POE oleylether.

The content of the non-ionic surfactant is not particularly limited and may be appropriately selected according to the purpose. However, it is preferably from 2 parts by mass to 7 parts by mass relative to 100 parts by mass of the thermoplastic material. When the content is less than 2 parts by mass, the effect of making the particle diameter of the aqueous emulsion of the thermoplastic material small may be poor when making an aqueous emulsion of the thermoplastic material. When the content is greater than 7 parts by mass, the flow path wall 12y forming layer may become soft to degrade the friction resistance of the flow path wall 12y.

—Colorant—

The colorant may be added in order to impart the function for enabling the flow path wall 12y to be distinguished in the flow path member 12. The colorant is not particularly limited, and an appropriate one may be selected according to the purpose. Examples thereof include carbon black, azo-based pigment, phthalocyanine, quinacridone, anthraquinone, perylene, quinophthalone, aniline black, titanium oxide, zinc oxide, and chromium oxide. Among these, carbon black is preferable.

The content of the colorant is not particularly limited and may be appropriately selected according to the purpose. However, it is preferably from 0.5 parts by mass to 5 parts by mass relative to 100 parts by mass of the thermoplastic material.

The shape of the flow path wall 12y is not particularly limited and may be appropriately selected according to the purpose. Examples thereof include one of a straight line, a curve, and a junction of a plurality of branches, or combinations of these.

The pattern width of the flow path wall 12y (the width of a wall portion) is not particularly limited, and patterning may be applied with an arbitrary width according to the size of the testing device 10. However, the width is preferably 500 μm or greater. When the pattern width is less than 500 μm, the voids in the hydrophilic porous base member may be insufficiently filled with the hydrophobizing materials, which may make the flow path wall fail to function as a liquid-impenetrable barrier.

According to an embodiment of the present invention, the flow path wall 12y may be formed to have an arbitrary length in the direction of thickness of the hydrophilic porous material from the surface thereof into the interior thereof, i.e., in the direction of depth. Factors that control the length include the melt viscosity and the hydrophilicity of the fat and oil or the thermoplastic resin. The lower the melt viscosity, the easier it becomes for the fat and oil or the thermoplastic resin to penetrate into the interior of the hydrophilic porous material from the surface thereof, which enables a long length. Conversely, the higher the melt viscosity, the harder it becomes for the fat and oil or the thermoplastic resin to penetrate into the interior of the hydrophilic porous material from the surface thereof, which enables a substantially non-penetrated state. It is possible to control the thickness by controlling the melt viscosity.

Meanwhile, as for the hydrophilicity of the fat and oil and the thermoplastic resin, ones with a higher hydrophilicity can more easily penetrate into the interior of the hydrophilic porous material from the surface thereof, which enables a long length. Conversely, ones with a lower hydrophilicity can more hardly penetrate into the interior of the hydrophilic porous material from the surface thereof, which enables a substantially non-penetrated state. It is possible to control the thickness by controlling the hydrophilicity, but the melt viscosity influences the penetrability much more than the hydrophilicity does.

The melt viscosity of the thermoplastic material varies depending also on the hydrophilicity of the hydrophilic porous material, or the fat and oil or the thermoplastic resin. Therefore, the value range of the melt viscosity to be mentioned below does not necessarily apply, but the thermoplastic material (the fat and oil, and the thermoplastic resin), if it is used in a hydrophilic porous base member such as cellulose, can be arbitrarily selected from materials of a very broad viscosity range of from 3 mPa·s to 1,600 mPa·s, and can be thermally transferred. In particular, in order to make the flow path wall forming materials penetrate into the interior of the hydrophilic porous material from the surface thereof so as to make the length of the flow path wall in the direction of thickness large, it is preferable to use a thermoplastic material having a melt viscosity of from 6 mPa·s to 200 mPa·s.

Meanwhile, conventional techniques include an inkjet system. For example, an inkjet printer using an ultraviolet curable resin ink discharges the ink from the head and makes the ink droplets fly and land into a porous layer. Therefore, there is a limitation; in order for a liquid to be discharged from the head, the viscosity of the liquid needs to be as low as 15 mPa·s at the maximum, or needs actually to be lower than 10 mPa·s, or otherwise the liquid cannot be discharged from the head, which allows poor latitude in the selection of the material. For this reason, the ink that can be used in the inkjet printer has a very low viscosity, and hence easily spreads in a porous layer, making a large bleed.

The same can be said for a wax printer. A wax printer thermally melts a solid ink and discharges the ink from the head to make droplets of the melted ink fly and land into a porous layer. Therefore, there is the same viscosity limitation as described above, in order for the ink to be discharged from the head, resulting in a poor latitude for the material. Besides, in the case of a wax printer, in reality, the temperature of the solid ink lowers during the flight to thereby make the viscosity have already risen above the level at which the ink can penetrate into the porous layer when the ink droplets land on the porous layer. Therefore, the ink droplets stop on the surface of the porous layer and cannot penetrate into the interior of the porous layer. This indispensably necessitates a step of heating the porous layer to a temperature at which the thermoplastic material can melt sufficiently in order to make the material penetrate. Therefore, not only does the process become complicated, but the porous layer cannot avoid being entirely heated, which makes it easier for the ink to spread also in the horizontal direction, making a large bleed.

In contrast, the thermal transfer system performs printing by bringing the thermal head into direct contact with a porous layer via the transfer member for flow path wall formation. Therefore, the thermal head applies heat only locally to a minute portion to which to transfer the ink, which enables effective suppression of the spreading of the thermoplastic material in the horizontal direction, resulting in a highly linear flow path with no bleed.

The length can also be controlled by controlling the energy to be applied for thermal compression bonding. That is, the more the energy to be applied is increased to raise the temperature of the fat and oil, and the thermoplastic resin, which are the thermoplastic material, the more inward they penetrate, whereas the more the temperature is lowered, the closer to the surface they stop.

<<Reaction Field>>

Reaction fields (R1, R2, and R3) are provided in the porous portion 12x of the flow path member 12 for reactions of an analyte liquid and a reagent. In the testing device 10 shown in FIG. 1 to FIG. 3, the reaction field R1 is a region in which to elute the antibody applied in the reaction field R1 from the porous base member to let it undergo an antigen-antibody reaction with an antigen in the analyte liquid. The reaction field R2 is a region in which to provide a test line for trapping an antigen-labeled antibody linkage formed in the reaction field R1 and showing a color reaction. The reaction field R3 is a control line for trapping a labeled antibody and showing a color reaction, which is provided for the purpose of confirming whether the analyte liquid has reached the reaction field R3 infallibly.

The reagent placed in the reaction field R1 is not particularly limited, and examples thereof include a gold colloid-labeled antibody such as gold colloid-labeled anti-human IgG.

The reagent placed in the reaction field R2 is not particularly limited, and examples thereof include anti-human IgG.

The reagent placed in the reaction field R3 is not particularly limited, and examples thereof include human IgG.

The reaction fields (R1, R2, and R3) are formed by the reagents described above being placed in the pores (flow paths) of the porous portion 12x by such a method as coating, etc.

<<Adhesive Layer>>

If a pollutant is mixed in a chromatography assay as the testing device 10, e.g., in a biochemical immunochromatography assay, a normal antigen-antibody reaction will not occur, and a correct diagnosis result will not be obtained. Therefore, a very clean condition is required in an immunochromatography assay. Conventionally, in fabrication of a testing device, an adhesive has been used as a means for integrating a hydrophilic porous material and a base sheet made of paper. However, where the adhesive is used, there have been some cases where the adhesive penetrates into the hydrophilic porous material and contaminates the hydrophilic porous material. Hence, such a testing device has not been suitable for use as an immunochromatography assay. Further, it has been necessary to perform a step of drying the moisture contained in the adhesive, which has complicated the fabrication process.

In the present embodiment, the constituent material of the adhesive layer 15 is not particularly limited. However, it may be a thermoplastic material, which is preferably a hydrophobic thermoplastic material and more preferably a hot-melt adhesive. When a thermoplastic material is selected as the adhesive layer 15, it is possible to bond the base member 11 and the flow path member 12 with each other by the simple method of hot-melt bonding. This improves the adhesive strength and makes the testing device 10 suitable for use in a fieldwork. This also makes it less likely for the constituent material of the adhesive layer 15 to penetrate into the hydrophilic porous material, and hence can prevent the hydrophilic porous material from being polluted. Furthermore, this makes it less likely for the adhesive to be eluted when an analyte liquid is dropped into the flow path member 12.

Specific examples of the thermoplastic material used as the adhesive layer 15 include but are not particularly limited to a polyester resin, a styrene/acrylic copolymer resin, an ethylene vinyl acetate resin, a polyamide resin, a polyolefin resin, and a polyurethane resin.

<<Viscous Layer>>

In the testing device 10 shown in FIG. 1 to FIG. 3, the viscous layer 16 is provided on a side of the base member 11 opposite to the side thereof contacting the adhesive layer 15. With the viscous layer 16 provided on one side of the base member 11, it becomes less easy for the testing device 10 to be blown away by a wind when the testing device 10 is used outdoors. The viscosity of the viscous layer 16 is not particularly limited, but is preferably from 2 N/20 mm to 10 N/20 mm, and more preferably from 3 N/20 mm to 8 N/20 mm. When the viscosity is greater than 10 N/20 mm, the viscous layer may not be easily peeled from a surface to which it is bonded, and in some case, peeling may occur at any other bonding interface of the device. When the viscosity is less than 2 N/20 mm, the viscous layer may have insufficient viscosity and may not perform its function to thereby let the device be blown away by a wind. The viscosity is measured according to peeling adhesive force measurement. The measurement is performed according to ISO29862, by peeling a sheet having a width of 20 mm, at a tensile speed of 300 mm/min. All measurements are performed under conditions environmentally controlled at room temperature (23° C.) (relative humidity to air of 50%). The constituent material of the viscous layer 16 is not particularly limited, and examples thereof include elastomers such as various natural rubbers, an acrylic acid ester copolymer, a silicone rubber, and various urethane resins.

<<Absorbent Member>>

The absorbent member 14 is not particularly limited, except that it should be able to absorb water, and a material thereof may be selected from publicly-known materials. Examples of the material of the absorbent member 14 include paper, fiber such as fabric, a polymeric compound having a carboxyl group or a salt thereof, a partially cross-linked product of a polymeric compound having a carboxyl group or a salt thereof, and a partially cross-linked product of a polysaccharide.

<<Barrier Member>>

In the present embodiment, the barrier member 13 contacts the flow path wall 12y of the flow path member 12 and the absorbent member 14, and covers at least a portion of the flow path member 12. The barrier member 13 has a barrier property against water, and preferably has a gas barrier property. Having a gas barrier property means that the barrier member has a smaller gas permeability than that of at least paper. Preferable examples of the constituent material of the barrier member 13 include materials such as a film and a laminate that have a water gas permeability (water vapor permeability) of 100 g/(m$^2$·day) or less, preferably 50 g/(m$^2$·day) or less, and more preferably 10 g/(m$^2$·day) or less, where the water gas permeability is measured according to ISO15106-1. Examples of materials having a water gas permeability of 50 include a polyethylene wax, a polypropylene wax, a silicone resin, polycarbonate, and polystyrene. The thickness of the barrier member 13 is not particularly limited. However, it is preferably from 5 μm to 100 μm, and more preferably from 10 μm to 70 μm. When the thickness is less than 5 μm, the barrier member may not be able to have a sufficient gas shielding property to thereby promote drying over time. When the thickness is greater than 100 μm, the barrier member may have a poor adhesiveness with respect to the flow path member.

Use of the barrier member 13 in this way prevents a hand from being contaminated when touching the testing device 10. Therefore, the testing device requires no housing.

A material preferable as the material of the barrier member 13 is not particularly limited, and examples thereof include waxes such a candelilla wax, polyamides such as nylon, and resins such as an ethylene/vinyl alcohol copolymer resin (EVOH) and a polyvinylidene chloride resin. These materials have thermoplasticity, and are preferable in thermal transferability, a film forming property, or the like. When the material of the barrier member is the same as the flow path wall forming materials described later, melt adhesiveness between the flow path wall 12y and the barrier member 13 can be enhanced. Among the materials described above, the waxes such as a candelilla wax are preferable in terms of releasability during thermal transfer. Note that resins are preferable when a gas barrier property is required.

In the present embodiment, an opening 13a from which to drop an analyte liquid is formed in the barrier member 13. In order to prevent the flow path from absorbing moisture during storage of the testing device 10, the opening 13a may be sealed with a publicly-known seal member. Examples of such a seal member include a PVC film containing a water-soluble acrylic resin in its adhesive layer, an example of which is FILMOLUX 609 (with a thickness of 70 μm) manufactured by Filmolux Co., Ltd. For example, when the whole of the testing device 10 is hermetically sealed for storage, a seal member may not need to be provided.

<<Transfer Member for Flow Path Wall Formation>>

Figure 4:
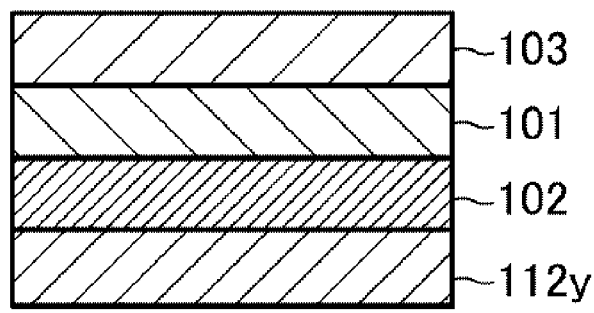
FIG. 4 is a cross-sectional diagram of a transfer member for flow path wall formation according to an embodiment of the present invention.

Next, a method for forming the flow path member 12 by transferring the flow path wall forming materials into the hydrophilic porous material will be explained. First, the transfer member for flow path wall formation will be explained with reference to FIG. 4. FIG. 4 is a cross-sectional diagram of the transfer member for flow path wall formation. The transfer member for flow path wall formation 100 is obtained by stacking a releasing layer 102 and a flow path wall forming layer 112y in this order over a support member 101, and includes other layers according to necessity.

<Support Member>

The shape, structure, size, material, etc. of the support member 101 are not particularly limited, and may be appropriately selected according to the purpose. The structure may be a single-layer structure, or may be a layered structure. The size of the support member may be appropriately selected according to the size of the testing device 10, etc.

The material of the support member 101 is not particularly limited, and may be appropriately selected according to the purpose. Examples thereof include polyester such as polyethylene terephthalate (PET) and polyethylene naphthalene (PEN), polycarbonate, a polyimide resin (PI), polyamide, polyethylene, polypropylene, polyvinyl chloride, polyvinylidene chloride, polystyrene, a styrene/acrylonitrile copolymer, and cellulose acetate One of these may be used alone, or two or more of these may be used in combination. Among these, polyethylene terephthalate (PET) and polyethylene naphthalate (PEN) are particularly preferable.

It is preferable to perform a surface activation treatment on the surface of the support member 101, in order to improve close adhesiveness with respect to the layer to be provided over the support member 101. Examples of the surface activation treatment include a glow discharge treatment, and a corona discharge treatment.

The support member 101 may be kept after having transferred the flow path wall forming layer 112y into the hydrophilic porous material. Alternatively, the support member 101, etc. may be peeled and removed by means of the releasing layer 102, after having transferred the flow path wall forming layer 112y. The support member 101 is not particularly limited, and may be an appropriately synthesized product or may be a commercially available product. The average thickness of the support member 101 is not particularly limited and may be appropriately selected according to the purpose. However, it is preferably from 3 µm to 50 µm.

<Releasing Layer>

The releasing layer 102 has a function of improving separability between the support member 101 and the flow path wall forming layer 112y during transfer. The releasing layer 102 also has a function of thermally melting to a low viscosity liquid when heated with a heating/pressurizing unit such as a thermal head to thereby make it easier for the flow path wall forming layer 112y to be separated at the interface between the heated portion and a non-heated portion. The releasing layer 102 contains a wax and a binder resin, and further contains other components appropriately selected according to the purpose.

—Wax—

The wax is not particularly limited, and an appropriate one may be selected according to the purpose. Examples thereof include: natural wax such as beeswax, carnauba wax, spermaceti, Japan tallow, candelilla wax, rice wax, and montan wax; synthetic wax such as paraffin wax, microcrystalline wax, oxide wax, ozokerite, ceresin, ester wax, polyethylene wax, and polyethylene oxide wax; higher fatty acid such as margaric acid, lauric acid, myristic acid, palmitic acid, stearic acid, furoic acid, and behenic acid; higher alcohol such as stearin alcohol and behenyl alcohol; esters such as sorbitan fatty acid ester; and amides such as stearamide and oleic amide. One of these may be used alone or two or more of these may be used in combination. Among these, carnauba wax and polyethylene wax are preferable because they are excellent in releasability.

—Binder Resin—

The binder resin is not particularly limited, and an appropriate one may be selected according to the purpose. Examples thereof include an ethylene/vinyl acetate copolymer, a partially saponified ethylene/vinyl acetate copolymer, an ethylene/vinyl alcohol copolymer, an ethylene/sodium methacrylate copolymer, polyamide, polyester, polyurethane, polyvinyl alcohol, methyl cellulose, carboxymethyl cellulose, starch, polyacrylic acid, an isobutylene/maleic acid copolymer, a styrene/maleic acid copolymer, polyacrylamide, polyvinyl acetal, polyvinyl chloride, polyvinylidene chloride, an isoprene rubber, a styrene/butadiene copolymer, an ethylene/propylene copolymer, a butyl rubber, and an acrylonitrile/butadiene copolymer. One of these may be used alone, or two or more of these may be used in combination.

The method for forming the releasing layer 102 is not particularly limited, and an appropriate method may be selected according to the purpose. Examples thereof include a hot-melt coating method, and a coating method using a coating liquid obtained by dispersing the wax and the binder resin in a solvent. The average thickness of the releasing layer 102 is not particularly limited and may be appropriately selected according to the purpose. However, it is preferably from 0.5 µm to 2.0 µm. The amount of deposition of the releasing layer 102 is not particularly limited and may be appropriately selected according to the purpose. However, it is preferably from 0.5 g/m$^2$ to 8 g/cm$^2$, and more preferably from 1 g/m$^2$ to 5 g/m$^2$.

<Flow Path Wall Forming Layer>

The materials, etc. of the flow path wall forming layer 112y are as described above as for the flow path wall forming materials. The method for forming the flow path wall forming layer 112y is not particularly limited, and an appropriate method may be selected according to the purpose. For example, as a hot-melt coating method or a coating method using a coating liquid obtained by dispersing the wax and the binder resin in a solvent, a common coating method using a gravure coater, a wire bar coater, a roll coater, or the like may be used. According to such a method, the support member 101 or the releasing layer 102 is coated with the flow path wall forming layer coating liquid. When the liquid is dried, the flow path wall forming layer is formed.

The average thickness of the flow path wall forming layer 112y is not particularly limited and may be appropriately selected according to the purpose. However, it is preferably from 5 µm to 250 µm. When the average thickness is less than 5 µm, the amount of the flow path wall forming layer 112y may be insufficient for filling the voids in the hydrophilic porous material. When the average thickness is greater than 250 µm, it becomes harder for heat from the thermal head to be conducted through the flow path wall forming layer 112y, to thereby degrade the transferability.

The amount of deposition of the flow path wall forming layer 112y is not particularly limited and may be appropriately selected according to the purpose. However, it is preferably from 5 g/m$^2$ to 250.0 g/m$^2$, and more preferably from 30 g/m$^2$ to 150.0 g/m$^2$.

<Other Layers and Members>

The other layers and members are not particularly limited, and appropriate ones may be selected according to the purpose. Examples thereof include a back layer 103, an undercoat layer, and a protection film.

—Back Layer—

It is preferable that the transfer member for flow path wall formation 100 include a back layer 103 over a side of the support member 101 opposite to a side thereof over which the flow path wall forming layer 112y is formed. Heat is directly applied to this opposite side by a thermal head or the like at a position corresponding to the shape of the flow path wall. Therefore, it is preferable that the back layer 103 have resistance to high heat and resistance to friction with a thermal head or the like. The back layer 103 contains a binder resin, and further contains other components according to necessity.

The binder resin is not particularly limited, and an appropriate one may be selected according to the purpose. Examples thereof include a silicone-modified urethane resin, a silicone-modified acrylic resin, a silicone resin, a silicone rubber, a fluororesin, a polyimide resin, an epoxy resin, a phenol resin, a melamine resin, and nitrocellulose. One of these may be used alone or two or more of these may be used in combination.

The other components are not particularly limited, and appropriate ones may be selected according to the purpose. Examples thereof include inorganic particles of talc, silica, and organopolysiloxane, etc., and a lubricant.

The method for forming the back layer 103 is not particularly limited, and an appropriate method may be selected according to the purpose. Examples thereof include common coating methods using a gravure coater, a wire bar coater, and a roll coater, etc. The average thickness of the back layer 103 is not particularly limited and may be appropriately selected according to the purpose. However, it is preferably from 0.01 µm to 1.0 µm.

—Undercoat Layer—

An undercoat layer may be provided between the support member 101 and the flow path wall forming layer 112y, or between the releasing layer 102 and the flow path wall forming layer 112y. The undercoat layer contains a resin, and further contains other components according to necessity. The resin is not particularly limited, and an appropriate one may be selected according to the purpose. The resin may be any of the resins usable for the flow path wall forming layer 112y and the releasing layer 102.

—Protection Film—

It is preferable to provide a protection film over the flow path wall forming layer 112y for protecting the layer from contamination or damages during storage. The material of the protection film is not particularly limited, and an appropriate one may be selected according to the purpose, as long as it can be easily separated from the flow path wall forming layer 112y. Examples thereof include silicone sheet, polyolefin sheet such as polypropylene sheet, and polytetrafluoroethylene sheet. The average thickness of the protection film is not particularly limited and may be appropriately selected according to the purpose. However, it is preferably from 5 µm to 100 µm, and more preferably from 10 µm to 30 µm.

<Transfer of Flow Path Wall Forming Layer>

In the formation of the flow path wall 12y, a hydrophilic porous material side of a receiving member for flow path wall formation that contains the base member 11, the hydrophilic porous material (an example of a porous layer), and the adhesive layer 15 bonding the base member 11 with the hydrophilic porous material is faced and overlapped with the flow path wall forming layer 112y side of the transfer member for flow path wall formation 100. Then, heat having a temperature lower than the heatproof temperature of the base member 11 is applied to the flow path wall forming layer 112y of the transfer member for flow path wall formation 100 in order to melt the flow path wall forming layer 112y and transfer it into the hydrophilic porous material, to thereby form a partition wall in the hydrophilic porous material. In this case, it is possible to form a flow path having a desired pattern, by applying heat with a desired pattern to the transfer member for flow path wall formation 100.

The method for thermally transferring the flow path wall forming layer 112y is not particularly limited, and an appropriate method may be selected according to the purpose. Examples thereof include a method of melting and transferring the flow path wall forming layer 112y by thermal compression bonding with a serial thermal head, a line thermal head, etc. The energy applied in the thermal compression bonding is not particularly limited, and may be appropriately selected according to the purpose. However, it is preferably from 0.1 mJ/dot to 1.00 mJ/dot. When the applied energy is lower than 0.1 mJ/dot, the flow path wall forming layer 112y may be melted insufficiently. When the applied energy is higher than 1.00 mJ/dot, portions of the transfer member for flow path wall formation 100 other than the flow path wall forming layer 112y may be melted and contaminate the thermal head.

<<Use Applications of Testing Device>>

The use applications of the testing device 10 are not particularly limited, and appropriate applications may be selected according to the purpose. Examples thereof include a chromatography assay as an analytical sheet widely applicable to chemical/biochemical analyses. Examples of such a testing device 10 include an immunochromatography assay, a biochemical sensor (a sensing chip) for blood testing and DNA testing, and a small-size analytical device (a chemical sensor) for quality control of foods and beverages.

A sample (analyte) to be used for biochemical testing is not particularly limited, and an appropriate one may be selected according to the purpose. Examples thereof include a pathogen such as a bacterium and a virus, blood, saliva, a lesional tissue, etc. separated from living organisms, and egestion such as enteruria. Further, for performing a prenatal diagnosis, the sample may be a part of a fetus cell in an amniotic fluid, or of a dividing egg cell in a test tube. Furthermore, these samples may be, after condensed to a sediment directly or by centrifugation or the like according to necessity, subjected to a pre-treatment for cell destruction through an enzymatic treatment, a thermal treatment, a surfactant treatment, and an ultrasonic treatment, any combinations of these, etc.

The testing device of the present embodiment also has a function of performing chromatography (separation and refinement) of an analyte liquid, because the porous portion 12x serves as a stationary phase. In this case, the porous portion 12x having a continuous cell of which internal wall has hydrophilicity serves as the stationary phase (a carrier). Different components in the analyte liquid flow through the flow paths at different speeds because of difference in their interactions with the stationary phase during the process of their penetration through the flow paths, i.e., difference in whether they are hydrophilic or hydrophobic.

A component having a higher hydrophilicity is more likely to adsorb to the porous portion 12x serving as the stationary phase, and repeats adsorbing and desorbing more times. Therefore, such a component penetrates through the flow paths at a lower speed. Conversely, a component having a higher hydrophobicity penetrates without adsorbing to the stationary phase. Therefore, such a component moves rapidly through the fluid paths. By utilizing the difference in the moving speed in the analyte liquid, and extracting the target component in the analyte liquid selectively and allowing it to undergo a reaction, it is possible to use the testing device 10 as a highly functional chemical or biochemical sensor.

<<Testing Method>>

A testing method using the testing device 10 is not particularly limited. Examples thereof include a method of dropping and supplying an analyte liquid containing an analyte into a dropping region 12c of the testing device 10, and making a judgment based on a reaction of the analyte flowing through the flow paths in the porous portion 12x with the reagents placed in the reaction fields (R1, R2, and R3). According to this testing method, a signal based on a reaction between the reagents and the analyte can be obtained obviously. Therefore, a judgment can be easily made.

The reaction field R1 elutes the antibody applied over the reaction field R1 from the porous base member to let it undergo an antigen-antibody reaction with the antigen in the analyte liquid. Then, the reaction field R2 traps an antigen-labeled antibody linkage formed in the reaction field R1, and the judgment is positive when the reaction field shows a color reaction upon the trapping. The reaction field R3 is a control line for trapping a labeled antibody and showing a color reaction, and it shows a color reaction when the analyte liquid has reached the reaction field R3 infallibly.

EXAMPLES

Examples of the present invention will be explained below. However, the present invention is not limited to these Examples by any means. In Examples and Comparative Examples described below, the voidage of the flow path member (porous portion) was calculated as follows.

<Calculation of Voidage of Porous Portion of Flow Path Member>

The voidage of the porous portion of the flow path member was calculated according to the calculation formula 1 below based on the basis weight (g/m²) and the thickness (μm) of the hydrophilic porous material, and the specific gravity of the component thereof.

Voidage (%)={1−[basis weight (g/m²)/thickness (μm)/specific gravity of the component]}×100    (Calculation Formula 1)

Example 1

Production of Base Member for Immunochromatography Assay

A polyester-based hot-melt adhesive (ALONMELT PES375S40 manufactured by Toagosei Co., Ltd.), as a thermoplastic resin, was heated to 190° C., and applied with a roll coater so as to have a thickness of 50 μm over a hydrophobic film applied-side of a cardboard (a white cardboard manufactured by C) Paper-Mitsuyama, with a basis weight of 270 g/m²), to one side of which a hydrophobic film (FILMOLUX 609 manufactured by Filmolux Co., Ltd., with a thickness of 70 μm) was bonded, to thereby form an adhesive layer. The applied product was kept stationary for 2 hours or longer. After this, a nitrocellulose membrane filter (HIFLOW PLUS HF135UBXSS manufactured by Merck Millipore Corporation, with a thickness of 135 μm and a voidage of 70%) was overlapped with the adhesive applied side, and a load of 1 kgf/cm² was applied to them at 150° C. for 10 seconds, to thereby obtain a base member for immunochromatography assay.

<Preparation of Flow Path Wall Forming Layer Coating Liquid>

An ester wax (WE-11 manufactured by NOF Corporation, with a melting start temperature of 65° C.) (100 parts by mass), montanic acid (product name: LUWAX-E manufactured by BASF Corporation, with a melting point of 76° C.) (2 parts by mass), and a long-chain alcohol represented by General Formula (1) below (where $R^1$ is an alkyl group having 28 to 38 carbon atoms, with a melting point of 75° C., manufactured by Nippon Seiro Co., Ltd.) (9 parts by mass) were dissolved at 120° C. After this, while they were stirred, morpholine (5 parts by mass) was added thereto. Then, hot water of 90° C. was dropped thereto in an amount that would result in a solid content of 30% by mass to form an oil-in-water emulsion. After this, the emulsion was cooled to thereby obtain an ester wax aqueous emulsion having a solid content of 30% by mass.

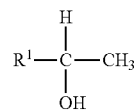

General Formula (1)

In General Formula (1), $R^1$ represents an alkyl group having 28 to 38 carbon atoms.

The average particle diameter of the obtained ester wax aqueous emulsion measured with a laser diffraction/scattering particle size distribution analyzer ("LA-920" manufactured by Horiba, Ltd.) was 0.4 μm.

Next, the obtained ester wax aqueous emulsion (with a solid content of 30% by mass) (100 parts by mass), and a carbon black water dispersion (FUJI SP BLACK 8625 manufactured by Fuji Pigment Co., Ltd., with a solid content of 30% by mass) (2 parts by mass) were mixed with each other, to thereby obtain a flow path wall forming layer coating liquid.

<Preparation of Releasing Layer Coating Liquid>

A polyethylene wax (POLYWAX 1000 manufactured by Toyo ADL Corporation, with a melting point of 99° C., and a needle penetration of 2 at 25° C.) (14 parts by mass), an ethylene/vinyl acetate copolymer (EV-150 manufactured by Du Pont-Mitsui Polychemicals Co., Ltd., with a weight average molecular weight of 2,100, and VAc of 21%) (6 parts by mass), toluene (60 parts by mass), and methyl ethyl ketone (20 parts by mass) were dispersed until the average particle diameter became 2.5 μm, to thereby obtain a releasing layer coating liquid.

<Preparation of Back Layer Coating Liquid>

A silicone-based rubber emulsion (KS779H manufactured by Shin-Etsu Chemical Co., Ltd., with a solid content of 30% by mass) (16.8 parts by mass), a chloroplatinic acid catalyst (0.2 parts by mass), and toluene (83 parts by mass) were mixed, to thereby obtain a back layer coating liquid.

<Production of Transfer Member for Flow Path Wall Formation>

The back layer coating liquid was applied over one side of a polyester film having an average thickness of 25 μm (LUMIRROR F65 manufactured by Toray Industries, Inc.) as a support member, and dried at 80° C. for 10 seconds, to thereby form a back layer having an average thickness of 0.02 μm.

Next, the releasing layer coating liquid was applied over a side of the polyester film opposite to the side over which the back layer was formed, and dried at 40° C. for 10 seconds, to thereby form a releasing layer having an average thickness of 1.5 μm. Next, the flow path wall forming layer coating liquid was applied over the releasing layer, and dried at 70° C. for 10 seconds, to thereby form a flow path wall forming layer having an average thickness of 100 μm. In this way, a transfer member for flow path wall formation of Example 1 was produced.

<Blocking Treatment>

A blocking treatment described below was applied to the base member for immunochromatography assay described above. The nitrocellulose membrane filter was immersed in a blocking agent (a BSA-containing PBS solution (with pH of 7.4), P3688-10PAK manufactured by Sigma-Aldrich Co., LLC), and shaken gently for 20 minutes. After this, any excess moisture on the surface of the filter was sucked way, and the filter was dried at room temperature.

<Formation of Flow Path Wall by Thermal Transfer>

The produced transfer member for flow path wall formation and the blocking treatment-applied base member were faced and overlapped with each other. After this, with a thermal transfer printer described below, thermal transfer was performed under pattern formation conditions described below, to thereby form a flow path wall having a width of 700 μm shown in FIG. 5.

For the formation of the flow path wall, printing was performed by constructing an evaluation system with a thermal head having a head density of 300 dpi (manufactured by TDK Corporation), at a printing speed of 16.9 mm/sec, and with a printing energy of 0.81 mJ/dot.

<Preparation of Absorbent Member Formation Coating Liquid>

A highly water-absorbent resin (AQUAKEEP 10SH-NF manufactured by Sumitomo Seika Chemicals, Co., Ltd., with a particle diameter of 25 μm) (20 parts by mass) as a water-absorbent polymer, polyethylene oxide (ALKOX L-6 manufactured by Meisei Chemical Works, Ltd.) (25 parts by mass) as a hydrophilic polymer, and ethanol (manufactured by Kanto Kagaku Ptd. Ltd., special grade) (60 parts by mass) were dissolved and stirred at room temperature (25° C.), to thereby produce a water-absorbent layer coating liquid having a resin solid content of 43% by mass.

<Production of Transfer Member for Absorbent Member Formation>

The back layer coating liquid was applied over one side of a polyester film having an average thickness of 25 μm (LUMIRROR F65 manufactured by Toray Industries, Inc.) as a support member, and dried at 80° C. for 10 seconds, to thereby form a back layer having an average thickness of 0.02 μm.

Next, the releasing layer coating liquid described above was applied over a side of the polyester film opposite to the side over which the back layer was formed, and dried at 40° C. for 10 seconds, to thereby form a releasing layer having an average thickness of 1.5 μm.

Next, the absorbent member formation coating liquid was applied over the releasing layer, and dried at 70° C. for 10 seconds, to thereby form an absorbent member forming layer having an average thickness of 100 μm. In this way, a transfer member for absorbent member formation was produced.

<Formation of Absorbent Member by Thermal Transfer>

Next, the transfer member for absorbent member formation produced in Example 1 and a side of the fluidic device over which the flow path member was formed were faced and overlapped with each other. Then, with the same thermal transfer printer as described above, thermal transfer was performed under pattern formation conditions described below, to thereby produce an absorbent member having a thickness of 100 μm shown in FIG. 5.

For the formation of the absorbent member, printing was performed by constructing an evaluation system with a thermal head having a head density of 300 dpi (manufactured by TDK Corporation), at a printing speed of 16.9 mm/sec, and with a printing energy of 0.28 mJ/dot.

<Production of Transfer Member for Reagent Composition Formation>

—Preparation of Reagent Composition Forming Layer Coating Liquid 1 (Test Line)—

Polyethylene oxide (ALKOX L-6 manufactured by Meisei Chemical Works, Ltd.) (10 parts by mass) as a hydrophilic resin, and an anti-human IgG antibody (4.7 mg/mL, 11886 manufactured by Sigma-Aldrich Co., LLC) (10 parts by mass) were dissolved and dispersed at room temperature (25° C.), to thereby produce a reagent composition forming layer coating liquid 1.

—Preparation of Reagent Composition Forming Layer Coating Liquid 2 (Control Line)—

Polyethylene oxide (ALKOX L-6 manufactured by Meisei Chemical Works, Ltd.) (10 parts by mass) as a hydrophilic resin, and human IgG (4.8 mg/mL, I2511-10MG, manufactured by Sigma-Aldrich Co., LLC) (10 parts by mass) were dissolved and dispersed at room temperature (25° C.), to thereby produce a reagent composition forming layer coating liquid 2.

The back layer coating liquid was applied over one side of a polyester film having an average thickness of 4.5 μm (LUMIRROR F57 manufactured by Toray Industries, Inc.) as a support member, and dried at 80° C. for 10 seconds, to thereby form a back layer having an average thickness of 0.02 μm.

Next, the reagent composition forming layer coating liquid 1 was applied over a side of the polyester film opposite to the side over which the back layer was formed, and dried at room temperature for 60 minutes, to thereby form a reagent composition forming layer having an average thickness of 10 μm. In this way, a transfer member for reagent composition formation 1 was produced. In the same manner, the reagent composition forming layer coating liquid 2 was applied over a side of a polyester film opposite to a side over which a back layer was formed, and dried at room temperature for 60 minutes, to thereby form a reagent composition forming layer having an average thickness of 10 μm. In this way, a transfer member for reagent composition formation 2 was produced.

<Formation of Reagent Pattern by Thermal Transfer>

The transfer member for reagent composition formation 1 and a side of the fluidic device at which the flow path wall was formed were faced and overlapped with each other. After this, with the same thermal transfer printer as described above, thermal transfer was performed under pattern formation conditions described below, to thereby form a reagent pattern having a thickness of 10 μm and a line width of 1 mm as a test line in the reaction field R2 shown in FIG. 5. Under the same conditions, the transfer member for reagent composition formation 2 was thermally transferred, to thereby form a reagent pattern having a thickness of 10 μm and a line width of 1 mm as a control line in the reaction field R3.

For the formation of the reagent patterns, printing was performed by constructing an evaluation system with a thermal head having a head density of 300 dpi (manufactured by TDK Corporation), at a printing speed of 16.9 mm/sec, and with a printing energy of 0.28 mJ/dot.

Next, gold colloid-labeled anti-human IgG (Gold 40 nm, OD=15, manufactured by Bioassay Works, LLC) (5 μL) was applied over the reaction field R1 as a gold colloid-labeled antibody.

Figure 5:
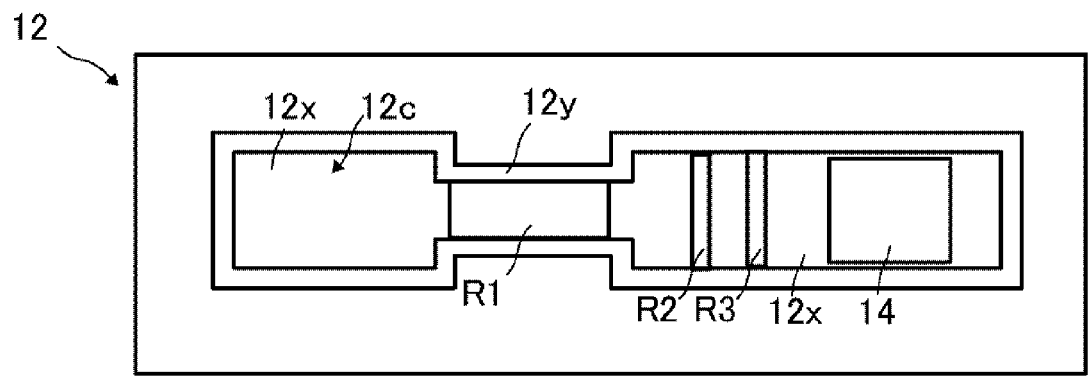
FIG. 5 is a plan view showing an example of a flow path member.
Figure 6:
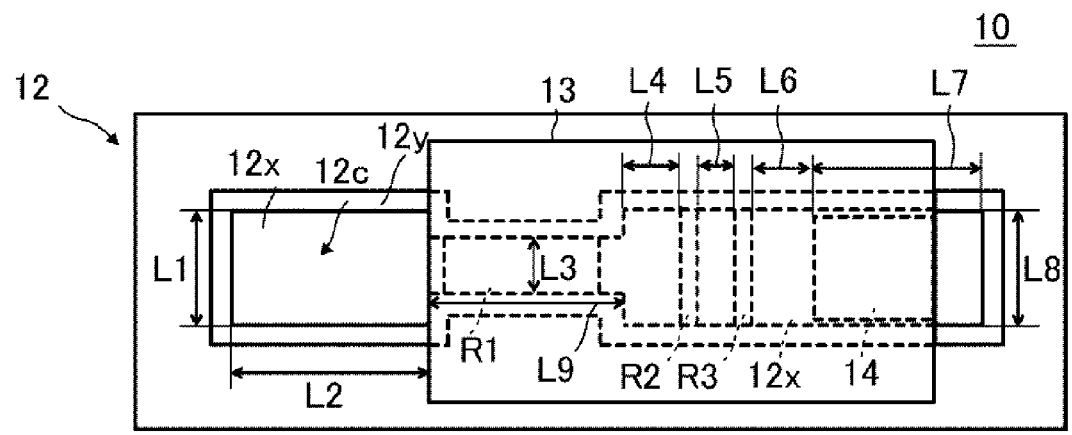
FIG. 6 is a plan view showing an example of a testing device.

Then, the transfer member for flow path wall formation was again faced and overlapped with the flow path member having the shape shown in FIG. 5. After this, with a thermal transfer printer, the barrier member 13 was formed under the printing conditions described above, to thereby obtain an immunochromatography assay shown in FIG. 6. The lengths L1 to L9 in FIG. 6 are as follows.

L1: 5 mm
L2: 17 mm
L3: 3 mm
L4: 5 mm
L5: 5 mm
L6: 5 mm
L7: 17 mm
L8: 5 mm
L9: 17 mm

<Blowing Test of Immunochromatography Assay>

Figure 7:
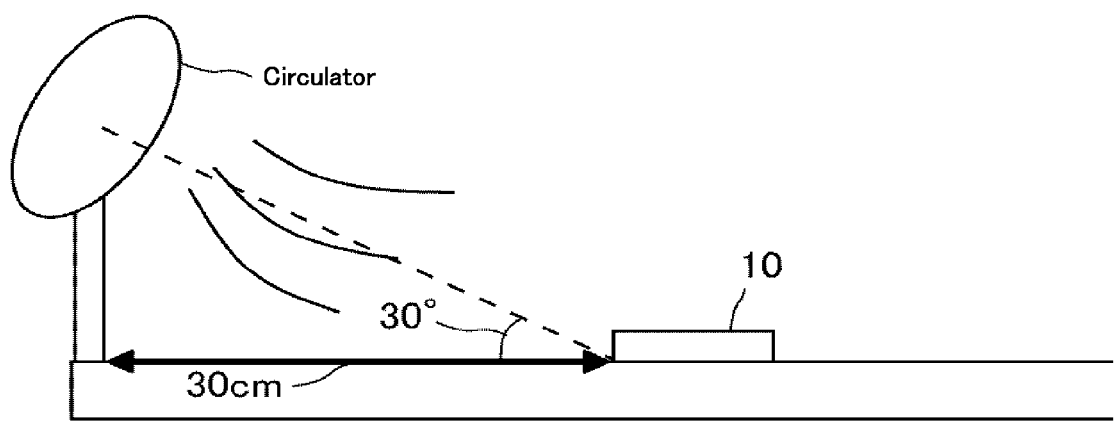
FIG. 7 is a conceptual diagram of an experimental system.

With an experimental system shown in FIG. 7, a wind having an air volume of 17.0 m$^3$/min, and a wind speed of 140 m/min was delivered for 5 minutes. FIG. 7 is a conceptual diagram of the experimental system. The circulator was KJ-d992W (manufactured by Twinbird Corporation). The stability of the immunochromatography assay (whether it would be flipped over or not) in this experiment was evaluated based on the following criteria. The result is shown in Table 1-1.

(Evaluation Criteria)

A: The assay was neither moved nor flipped over by the wind.

B: The assay was moved, but not flipped over by the wind.

C: The assay was flipped over by the wind.

<Adhesiveness Evaluation>

Water (30 μL) was dropped into the dropping region 12c of the porous portion, and the device was kept stationary for 20 minutes under conditions environmentally controlled at room temperature (23° C.) (relative humidity to air of 50%). After this, whether the flow path member 12 and the base member 11 could be peeled from each other was evaluated based on the criteria below, by trying to peel the flow path member 12 and the base member 11 from each other from their end at an angle of 90°.

(Evaluation Criteria)

A: They were not peeled from each other, and adhesiveness was very good.

B: They were peeled partially but remained usable, and adhesiveness was good.

C: They were peeled from each other completed, and adhesiveness was bad.

Example 2

An immunochromatography assay was fabricated and evaluated in the same manner as in Example 1 including the amount of use, except that polyester as the thermoplastic resin of Example 1 was changed to a modified olefin resin (PPET1008 manufactured by Toagosei Co., Ltd.). The heatproof temperature of the base member, the melting start temperature of the thermoplastic material, and the evaluation results are shown in Table 1-1.

Example 3

An immunochromatography assay was fabricated and evaluated in the same manner as in Example 1 including the amount of use, except that the cardboard as the base sheet of Example 1 was changed to Kent paper (BB KENT PAPER manufactured by Orion Co., Ltd., with a basis weight of 175 g/m$^2$). The heatproof temperature of the base member, the melting start temperature of the thermoplastic material, and the evaluation results are shown in Table 1-1.

Example 4

An immunochromatography assay was fabricated and evaluated in the same manner as in Example 1 including the amount of use, except that polyester as the thermoplastic resin of Example 1 was changed to a starch glue which was a water-soluble resin (FP200 manufactured by Fueki Nori Kogyo Co., Ltd.). The heatproof temperature of the base member, the melting start temperature of the thermoplastic material, and the evaluation results are shown in Table 1-1.

Example 5

An immunochromatography assay was fabricated and evaluated in the same manner as in Example 1 including the amount of use, except that polyester as the thermoplastic resin of Example 1 was changed to a polyvinyl alcohol (PVA) glue which was a water-soluble resin. The PVA glue was prepared as described below. The heatproof temperature of the base member, the melting start temperature of the thermoplastic material, and the evaluation results are shown in Table 1-1.

<Preparation of PVA Glue>

A 5% by mass aqueous solution of PVA (GOHSENOL N-300 manufactured by Nippon Synthetic Chemical Industry Co., Ltd.) was prepared. Then, this 5% by mass aqueous solution was dissolved at 95° C. to filter out the insoluble content, to thereby prepare a PVA glue.

Example 6

An immunochromatography assay was fabricated and evaluated in the same manner as in Example 1 including the amount of use, except that the cardboard as the base sheet of Example 1 was changed to regular paper (RICOPY COPY PAPER TYPE 6200 manufactured by Ricoh Company Limited, with a basis weight of 69 g/m$^2$). The heatproof temperature of the base member, the melting start temperature of the thermoplastic material, and the evaluation results are shown in Table 1-1.

Example 7

Fabrication of an immunochromatography was performed in the same manner as in Example 1 including the amount of use, except that the cardboard was changed to regular paper, and a spray glue (KONISHI BOND SPRAY GLUE Z-1 manufactured by Konishi Co., Ltd.) was sprayed uniformly over the full surface of a side of the regular paper of the immunochromatography assay opposite to a side thereof over which the porous layer was formed, from 30 cm away from the regular paper, and dried at room temperature (25° C.) for 20 seconds, to thereby fabricate an immunochromatography assay of Example 7, which was evaluated in the same manner as in Example 1. The adhesive strength was 2 N/20 mm. The heatproof temperature of the base member, the melting start temperature of the thermoplastic material, and the evaluation results are shown in Table 1-1.

Example 8

An immunochromatography assay was fabricated and evaluated in the same manner as in Example 1 including the amount of use, except that the cardboard of Example 1 was changed to regular paper (RICOPY COPY PAPER TYPE 6200 manufactured by Ricoh Company Limited, with a voidage of 50%), and the thermoplastic polyester resin was changed to a starch glue (FP200 manufactured by Fueki Nori Kogyo Co., Ltd.). The heatproof temperature of the base member, the melting start temperature of the thermoplastic material, and the evaluation results are shown in Table 1-1.

Example 9

An immunochromatography assay was fabricated and evaluated in the same manner as in Example 1 including the amount of use, except that the thermoplastic material in the flow path wall forming layer coating liquid was changed from the ester wax of Example 1 to a synthetic wax (DIACARNA manufactured by Mitsubishi Chemical Corporation, with a melting start temperature of 86° C.). The heatproof temperature of the base member, the melting start temperature of the thermoplastic material, and the evaluation results are shown in Table 1-1.

Example 10

An immunochromatography assay was fabricated and evaluated in the same manner as in Example 1 including the amount of use, except that the cardboard of Example 1 was changed to a polypropylene film (2500H TORAYFAN, a type having a thickness of 60 µm, manufactured by Toray Industries, Inc.). The heatproof temperature of the base member, the melting start temperature of the thermoplastic material, and the evaluation results are shown in Table 1-2.

Comparative Example 1

An immunochromatography assay was fabricated and evaluated in the same manner as in Example 1 including the amount of use, except that the base member for the immunochromatography assay of Example 1 was changed to a nitrocellulose membrane filter (HIFLOW PLUS HF135UBXSS manufactured by Merck Millipore Corporation, with a thickness of 135 µm, and a voidage of 70%), to one side of which a hydrophobic film (FILMOLUX 609 manufactured by Filmolux Co., Ltd., with a thickness of 70 µm) was bonded. In this case, because the immunochromatography assay did not have a base member (a support member), it was blown away by a wind easily in a blowing test. The heatproof temperature of the base member, the melting start temperature of the thermoplastic material, and the evaluation results are shown in Table 1-2.

Comparative Example 2

An immunochromatography assay was fabricated and evaluated in the same manner as in Example 1 including the amount of use, except that the cardboard of Example 1 was changed to a polypropylene film (LOW DENSITY PE EL, a type having a thickness of 300 µm, manufactured by Sekisui Seikei Co., Ltd.), and the thermoplastic material in the flow path wall forming layer coating liquid was changed from the ester wax of Example 1 to a synthetic wax (ITOWAX J550-S manufactured by Itoh Oil Chemicals Co., Ltd., with a melting start temperature of 142° C.). In this case, because the heatproof temperature of the polyethylene film which was the base member (support member) was lower than the melting start temperature of the synthetic wax which was the thermoplastic material, the base member thermally deformed during formation of the flow path wall by thermal transfer. Therefore, the formation of the flow path wall was incomplete, water dropped for the evaluations, etc. leaked to the outside of the flow path wall, and the fluidic device could not satisfy as a fluidic device. The heatproof temperature of the base member, the melting start temperature of the thermoplastic material, and the evaluation results are shown in Table 1-2.

TABLE 1-1

| No. | Base member (support member) | | | Flow path wall forming material (thermoplastic material) | | | Results | |
|---|---|---|---|---|---|---|---|---|
| | Kind | Basis weight (g/m²) | Heatproof temp. (° C.)/kind | Kind | Melting start temp. (° C.) | Adhesive Kind | Blowing test | Adhesiveness evaluation |
| Ex. 1 | Cardboard | 270 | 330/thermal decomposition | Ester wax | 65 | Thermoplastic polyester resin | A | A |
| Ex. 2 | Cardboard | 270 | 330/thermal decomposition | Ester wax | 65 | Thermoplastic modified olefin resin | A | A |
| Ex. 3 | Kent paper | 175 | 310/thermal decomposition | Ester wax | 65 | Thermoplastic polyester resin | A | A |
| Ex. 4 | Cardboard | 270 | 330/thermal decomposition | Ester wax | 65 | Starch glue (water-soluble resin) | A | B |
| Ex. 5 | Cardboard | 270 | 330/thermal decomposition | Ester wax | 65 | PVA glue (water-soluble resin) | A | B |

TABLE 1-1-continued

| | Base member (support member) | | | Flow path wall forming material (thermoplastic material) | | | Results | |
|---|---|---|---|---|---|---|---|---|
| No. | Kind | Basis weight (g/m²) | Heatproof temp. (° C.)/kind | Kind | Melting start temp. (° C.) | Adhesive Kind | Blowing test | Adhesiveness evaluation |
| Ex. 6 | Regular paper | 69 | 300/thermal decomposition | Ester wax | 65 | Thermoplastic polyester resin | B | A |
| Ex. 7 | Regular paper (with adhesiveness on back) | 69 | 300/thermal decomposition | Ester wax | 65 | Thermoplastic polyester resin | A | A |
| Ex. 8 | Regular paper | 69 | 300/thermal decomposition | Ester wax | 65 | Starch glue (water-soluble resin) | A | B |
| Ex. 9 | Cardboard | 270 | 330/thermal decomposition | Synthetic wax | 86 | Thermoplastic polyester resin | A | A |

TABLE 1-2

| | Base member (support member) | | | Flow path wall forming material (thermoplastic material) | | | Results | |
|---|---|---|---|---|---|---|---|---|
| No. | Kind | Basis weight (g/m²) | Heatproof temp. (° C.)/kind | Kind | Melting start temp. (° C.) | Adhesive Kind | Blowing test | Adhesiveness evaluation |
| Ex. 10 | Polypropylene film | 0.91 (*) | 168/VSP | Ester wax | 65 | Thermoplastic polyester resin | B | A |
| Comp. Ex. 1 | None | — | — | Ester wax | 65 | None | C | Un-evaluable |
| Comp. Ex. 2 | Polyethylene film | 0.92 (*) | 105/VSP | Synthetic wax | 142 | PVA glue (water-soluble resin) | C | C |

(*) In Example 10 and Comparative Example 2, measurements of specific gravity (to water of 4° C.) instead of basis weight were shown.

Aspects of the present invention are as follow, for example.

<1> A fluidic device, including;
a support member;
a porous layer; and
an adhesive layer bonding the support member and the porous layer with each other,
wherein a partition wall made of a thermoplastic material is formed in the porous layer, and
wherein the support member has a heatproof temperature that is higher than a melting start temperature of the thermoplastic material.

<2> The fluidic device according to <1>,
wherein the heatproof temperature of the support member is 180° C. or higher.

<3> The fluidic device according to <1> or <2>,
wherein the adhesive layer is a hydrophobic thermoplastic material.

<4> The fluidic device according to any one of <1> to <3>,
wherein the support member is a sheet of paper covered with a hydrophobic film.

<5> The fluidic device according to any one of <1> to <4>,
wherein a viscous layer is provided over a side of the support member opposite to a side thereof contacting the adhesive layer.

<6> The fluidic device according to <5>,
wherein the viscous layer has a viscosity of from 2 N/20 mm to 10 N/20 mm.

<7> The fluidic device according to any one of <1> to <6>,
wherein the support member has a basis weight of 170 g/m² or greater.

<8> A testing device, including:
the fluidic device according to any one of <1> to <7>,
wherein a reagent reactive with an analyte is placed over the porous layer.

<9> A method for fabricating a fluidic device, including:
overlapping a receiving member to which a thermoplastic material is to be transferred, with the thermoplastic material, wherein the receiving member is for flow path wall formation and includes a support member, a porous layer, and an adhesive layer bonding the support member and the porous layer with each other; and
applying heat having a temperature lower than a heatproof temperature of the support member to a transfer member to melt the thermoplastic material in the transfer member and transfer the thermoplastic material into the porous layer, to thereby form a partition wall in the porous layer.

This application claims priority to Japanese application No. 2013-194507, filed on Sep. 19, 2013 and incorporated herein by reference, and Japanese application No. 2014-181887, filed on Sep. 8, 2014 and incorporated herein by reference.

What is claimed is:

1. A fluidic device, comprising:
   a support member;
   a porous layer; and
   an adhesive layer bonding the support member and the porous layer with each other,
   wherein a partition wall made of a thermoplastic material is formed in the porous layer so that a part of the porous layer includes pores filled with the thermoplastic material, and
   wherein the support member has a heatproof temperature that is higher than a melting start temperature of the thermoplastic material.

2. The fluidic device according to claim 1,
   wherein the heatproof temperature of the support member is 180° C. or higher.

3. The fluidic device according to claim 1,
   wherein the adhesive layer is a hydrophobic thermoplastic material.

4. The fluidic device according to claim 1,
   wherein the support member is a sheet of paper covered with a hydrophobic film.

5. The fluidic device according to claim 1,
   wherein a viscous layer is provided over a side of the support member opposite to a side thereof contacting the adhesive layer.

6. The fluidic device according to claim 5,
   wherein the viscous layer has a viscosity of from 2 N/20 mm to 10 N/20 mm.

7. The fluidic device according to claim 1,
   wherein the support member has a basis weight of 170 g/m² or greater.

8. A testing device, comprising:
   the fluidic device according to claim 1,
   wherein a reagent reactive with an analyte is placed over the porous layer.

9. The fluidic device according to claim 1, wherein the part of the porous layer that includes the pores filled with the thermoplastic material is hydrophobized, and another part of the porous layer is not hydrophobized.

* * * * *